United States Patent [19]

Symington et al.

[11] Patent Number: 4,713,003

[45] Date of Patent: Dec. 15, 1987

[54] FIXTURE FOR ATTACHING PROSTHESIS TO BONE

[75] Inventors: John M. Symington, Etobicoke; Robin D. Listrom, Willowdale, both of Canada

[73] Assignee: University of Toronto Innovations Foundation, Toronto, Canada

[21] Appl. No.: 864,804

[22] Filed: May 19, 1986

[30] Foreign Application Priority Data

May 17, 1985 [CA] Canada ................................. 481851

[51] Int. Cl.4 ............................................. A61C 8/00
[52] U.S. Cl. ................................................... 433/173
[58] Field of Search ...................... 433/173, 179, 201.1

[56] References Cited

U.S. PATENT DOCUMENTS 3,797,113  3/1974  Branin .............................. 433/301.1
4,416,629  11/1983  Mozsary ............................. 433/174

Primary Examiner—Robert Peshock
Attorney, Agent, or Firm—Wyatt, Gerber, Shoup, Scobey and Badie

[57] ABSTRACT

A device is disclosed for use in connecting a prosthesis to bone such as connecting an artificial tooth or dental bridge to the jaws which comprises an implant portion or screw for connection to the bone, the screw having a head and a downwardly tapered shaft, an abutment portion for connection to the prothesis, and connecting means for connecting the implant and the abutment. Preferably, the components of the invention are machined from titanium alloy.

12 Claims, 9 Drawing Figures

FIG. 1

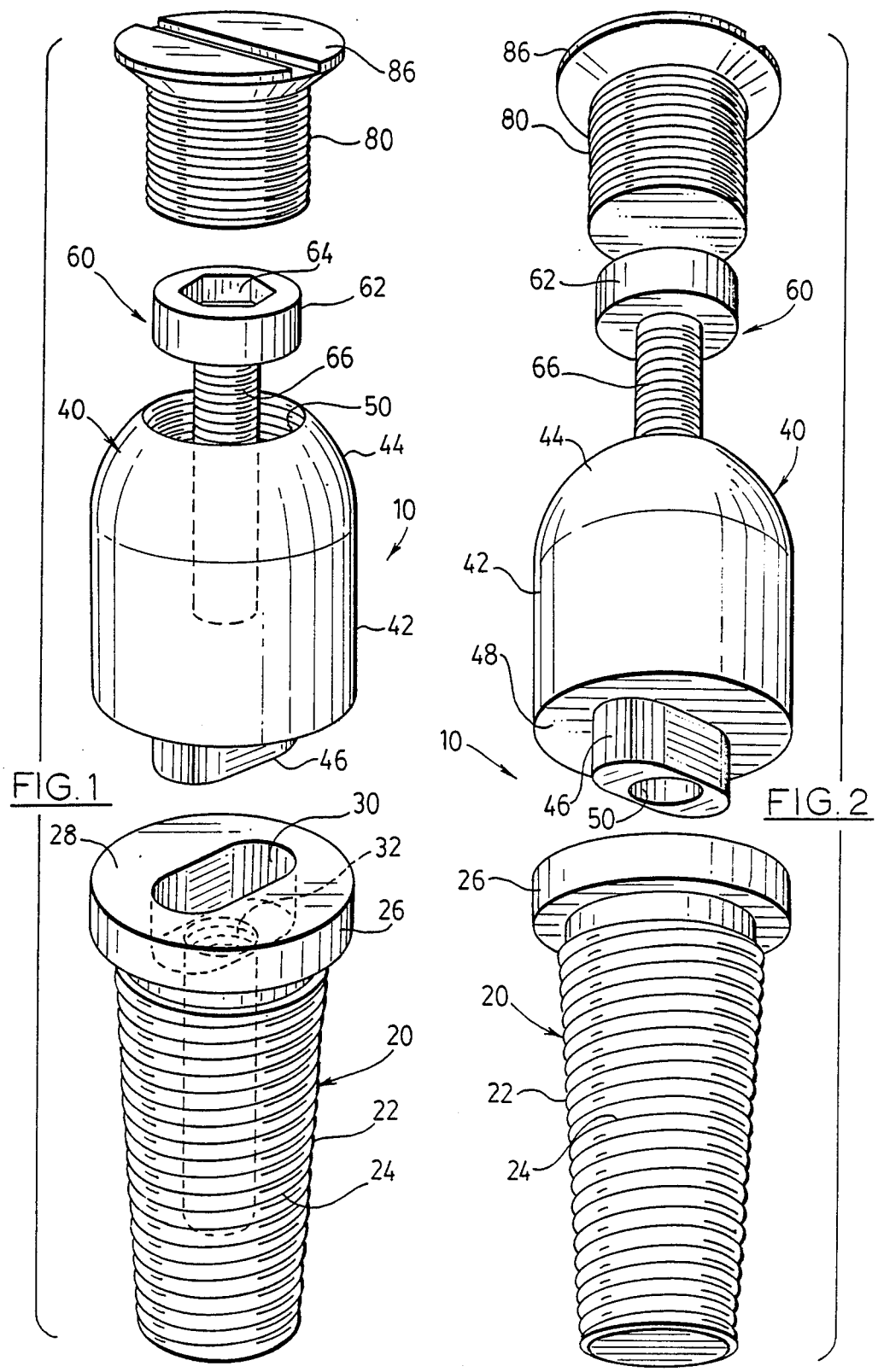

FIXTURE FOR ATTACHING PROSTHESIS TO BONE

FIELD OF THE INVENTION

This invention relates to devices which function to connect prosthesis and bone. One particular embodiment of the invention relates to such devices which function to anchor artificial teeth to the jaws.

BACKGROUND OF THE INVENTION

Devices of the type described herein are generally comprised of an implant portion which is anchored within bone and an abutment portion which supports the prosthesis and is connected to the implant. Important to the success of such devices is the rigid anchoring of the implant in the bone which is typically accomplished by providing a threaded hole in the bone to accommodate the implant. In this connection, the ability of the bone to accept and maintain the implant in situ is governed by a number of factors including resistance of the bone to fracturing both during drilling and insertion of the device and, importantly, transmission of loads acting on the device through the subsequently attached prothesis.

The specific problem of integrating teeth within the oral cavity by means other than superficial attachment has been addressed previously. One result is the proposal of Branemark as exemplified in *Int. J. Oral Sur.* 1981:10:387–416. In this proposal a generally cylindrical device is described which includes a number of connectable parts the majority of which are machined from substantially pure titanium.

Cylindrical implants, however, possess the disadvantage that they are unable to distribute evenly the forces derived from load bearing, e.g. during mastication, with the result that surrounding bone is unevenly stressed. It is desirable, therefore, to provide an implant which mitigates such undue stress so as to sustain generally the integrity of the bone surrounding the implant.

Thus it is an object of the present invention to provide a novel device for endosseous implantation which obviates or mitigates the above disadvantage.

SUMMARY OF THE INVENTION

To accomplish this objective, the present invention provides a device for connecting a prosthesis to bone which comprises an implant portion for integration with the bone, the implant being constituted by a screw having a shaft and a head, the shaft being tapered downwardly from the head; an abutment portion for integration with the prosthesis; and connecting means for coupling the implant portion with the abutment portion. Preferably, the implant and abutment of the present invention are machined from titanium alloy for example, an alloy including 6% aluminium and 4% vanadium.

The provision of the tapered screw results in enhanced distribution of stresses acting on the device in situ by increasing the relative surface area on which reaction forces can operate in response to impinging forces, as compared to the cylindrical implant known in the art.

In one preferred aspect of the present invention, the implant is self-tapping thus removing the requirement to thread the bone into which the implant is to be received.

While a variety of shapes of abutments may be used, depending on the particular environment within which they are used, in a second preferred aspect of the present invention the abutment is provided with a dome-shaped top, the advantages of which will be discussed in the following description.

In a third preferred aspect of the present invention a tongue and groove fitting is provided between the abutment and the implant, in addition to the connection means, to provide an additional mechanical interlock which inhibits relative rotation of the abutment and the implant after the two are mated.

Although it is not essential in all applications of the device, it is desirable, in certain circumstances, to adapt the abutment to receive a retaining screw, as will be evident in the following description.

BRIEF REFERENCE TO THE DRAWINGS

A specific preferred embodiment of the invention is illustrated in the accompanying drawings in which:

FIG. 1 represents a perspective exploded view of a preferred device according to the present invention showing the individual components as viewed at an angle from above;

FIG. 2 represents another exploded view of the device shown in FIG. 1 at an angle from below;

DESCRIPTION OF THE PREFERRED EMBODIMENTS

Figure 3:
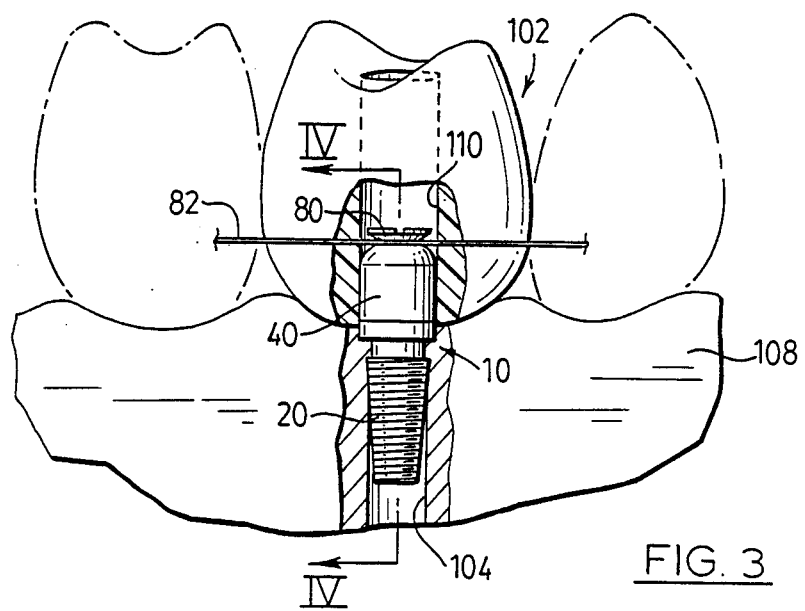
FIG. 3 represents a perspective side view of the embodiment illustrated in FIG. 1 showing the device in position within the mouth with a portion of the jaw broken away to show the implant.

Referring now to FIG. 1, there is illustrated a device 10 comprising an implant 20, an abutment 40, both of which are machined from a titanium alloy and a connecting screw 60, which is machined from stainless steel.

Implant 20 has a tapered body 22 bearing exterior self-tapping screw threads 24 and terminates in a head 26. The upper surface 28 of head 26 defines a generally elliptical recess 30 located centrally thereon. Implant 20 defines a longitudinal, centrally located bore 32 extending from recess 30 into but not through the tapered body 22. Bore 32 is screw-threaded to receive connecting screw 60. Preferably, the pitch of the threads 24 is about 16 turns per inch.

Abutment 40 is constituted by a cylindrical portion 42 which terminates in a dome-shaped part-spherical upper portion 44. The abutment is provided with protrusion 46 located centrally on its lower surface 48 as is more clearly illustrated in FIG. 2. The configuration of protrusion 46 is generally elliptical, i.e. complementary to recess 30 of implant 20. Mating of implant 20 and abutment 40 is effected by inserting the protrusion 46 into recess 30 until the lower surface 48 of the abutment is flush with the upper surface 28 of the implant. The provision of the generally elliptically shaped protrusion and recess provides a positive mechanical interlock which inhibits rotation of the abutment 40 about the protrusion 46 after mating. The abutment defines a bore 50 extending longitudinally through a central axis thereof from the domed upper portion 44 through the protrusion 46. Bore 50 aligns with bore 32 of implant 20 when the implant and the abutment are mated.

Figure 4:
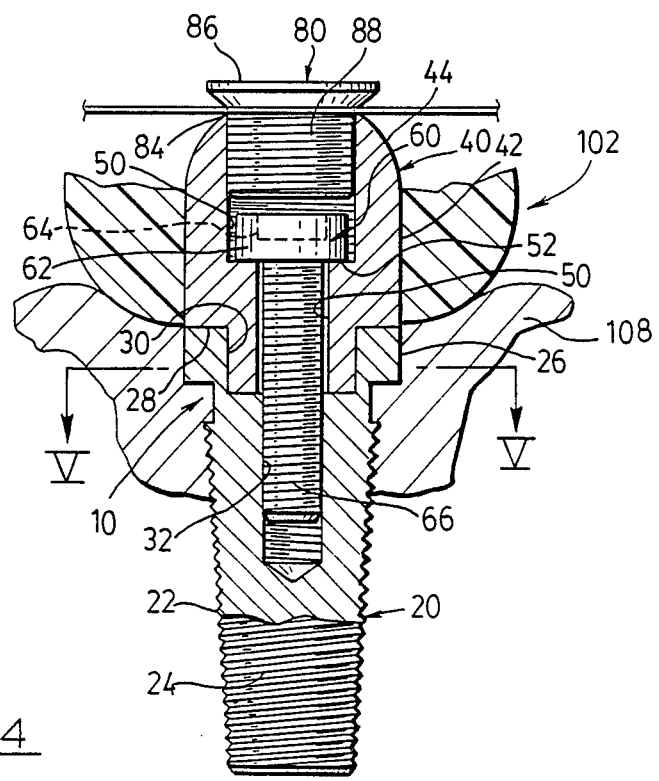
FIG. 4 represents a sectional side view along line IV—IV of FIG. 3.

Coupling of implant 20 and abutment 40 is achieved with connecting screw 60 and is best seen in FIG. 4. The connecting screw has a head 62 defining a hexagonal recess 64 to receive a driver, in this case an Allen key. A screw threaded shaft 66 extends from the head 62 for engagement along the length of bore 32 which, as mentioned, has complementary threading.

Figure 5:
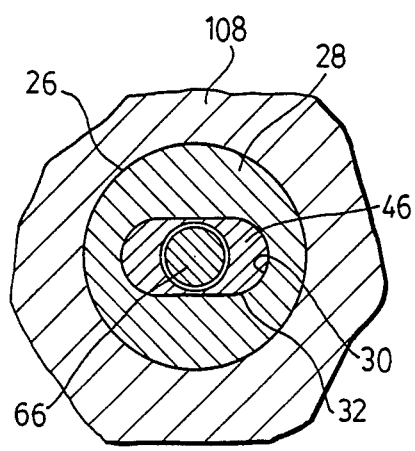
FIG. 5 represents a sectional view along lines V—V of FIG. 4 drawn on an enlarged scale.

Coupling may be achieved after implant 20 is mated with abutment 40 in the manner described above. It will be noted that the diameters of implant head 26 and abutment cylindrical portion 42 are equal resulting in uniform contour of the fixture above the tapered portion 22 when the implant and abutment are mated. With the abutment in place on the implant, connecting screw 60 is placed in bore 50 and driven into engagement with the aligned implant bore 32. A seat 52 is provided within abutment 40 coaxial with bore 50 to accomodate connecting screw head 62, and to prevent separation of the abutment and the implant, once the connecting screw is inserted. The driving of the connecting screw may, as mentioned be effected by an Allen key i.e. a right angle driver, thus providing the surgeon room enough to effect the driving action. FIG. 5 illustrates, in a sectional view, the relationship of the mated elements, the numerals representing like parts previously identified. In certain circumstances, it may be desirable to provide a retaining screw 80 (FIGS. 1 and 4) which is received within bore 50 at a location above the head 62 of connecting screw 60. If this is desired, bore 50 must be screw-threaded above seat 52 in order to engage complementary threads on retaining screw 80. Reference to this particular arrangement is discussed below.

The preceding description of the operative components and procedure by which the abutment and implant are connected has, for the sake of clarity, disregarded mention of any specific application of the device. In the following description, the device is described with particular reference to its utility as a means of coupling a dental prosthesis, i.e. a single artificial tooth or a dental bridge to the jaws.

Figure 6:
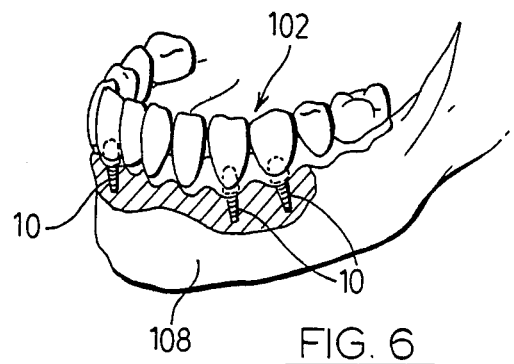
FIG. 6 represents a perspective view showing a plurality of devices positioned within the mouth for use in mounting a complement of artificial teeth.

To mount a complement of artificial teeth 102 onto a lower jaw 108, a plurality of devices 10 is positioned along the jaw, as is illustrated in FIG. 6. The positioning of each device 10, is described hereinafter with reference to FIG. 3.

A hole 104 is bored vertically into the jaw to receive the implant 20. The diameter of hole 104 is essentially at least less than the widest portion of the tapered body 22 and at least greater than its most narrow portion such that the tapered body 22 threadably engages the bone during insertion. The diameter of the hole 104 can, therefore, be selected to vary the number of turns required to drive the implant into a position in which head 26 abuts the surface of the jaw 108. The diameter of hole 104 should be selected, however, to ensure that the implant is sufficiently anchored and also to ensure that the bone into which it is threaded is not subject to undue stress exerted by the increasing diameter of the implant body. Notably, because the implant 20 is self-tapping, internal threading of the hole 104 is not required.

Once each implant is so positioned, a healing period is allowed to lapse whereafter an abutment 40 is coupled to each implant using a connecting screw 60, as described. A cast is then taken of the jaw 108 which details the exact positions of the abutments and provides the artisan with a substrate from which a suitable complement of teeth may be prepared. The advantages of providing a dome-shaped abutment are manifest at this particular stage of the process. Unless the known cylindrical implants are positioned to extend truly vertically from the jaw, the removal of the impression mould will cause distortion of the mould in the areas of the abutments, a result sometimes referred to as "dove tailing". In contrast, a certain degree of error is excused by the domed abutments of the preferred embodiment of the present invention since the domed contour will be cast substantially true where slight deviations from vertical have occurred during implantation.

Although the exact details of the method by which the complement of teeth is fashioned is not within the scope of the present invention, it will be noted that the teeth, usually acrylic, are typically supported on and are integral with a metal framework 82, details of which appear in the Branemark publication referred to above. At at least each of the positions corresponding to the locations of the respective implants, the framework is provided with apertures which communicate with both a hole 110 drilled into the acrylic teeth and bore 50 defined by the abutment. To locate the framework and, therefore, also to locate the teeth in position, a retaining screw 80 is driven into bore 50 which, in this particular embodiment, is screw-threaded to receive the retaining screw. Aperture 84 in the framework is of a diameter which effectively permits the shaft 88 of screw 80 to pass therethrough and threadably engage within bore 50 of the abutment while permitting the head 86 of screw 80 to trap the framework between the head and the abutment, once the screw is properly positioned. After each of the abutments has been coupled to the framework by a retaining screw in the manner described, it is common to fill each of holes 110 with a plastic to provide a suitable surface on the teeth.

It will be understood that the provision of a retaining screw and screw-threaded abutment bore 50 is not always required for successful application of the present invention. It is possible to fix the abutment to the tooth by other means such as by adhesive, etc. An example of an application in which a retaining screw is not essential, although it may be desirable is the use of a single device in connecting a single tooth to the jaw. In this particular embodiment, an adhesive may be applied to the surface of the abutment to bond the undersurface of the artificial tooth adequately thereto.

Figure 7:
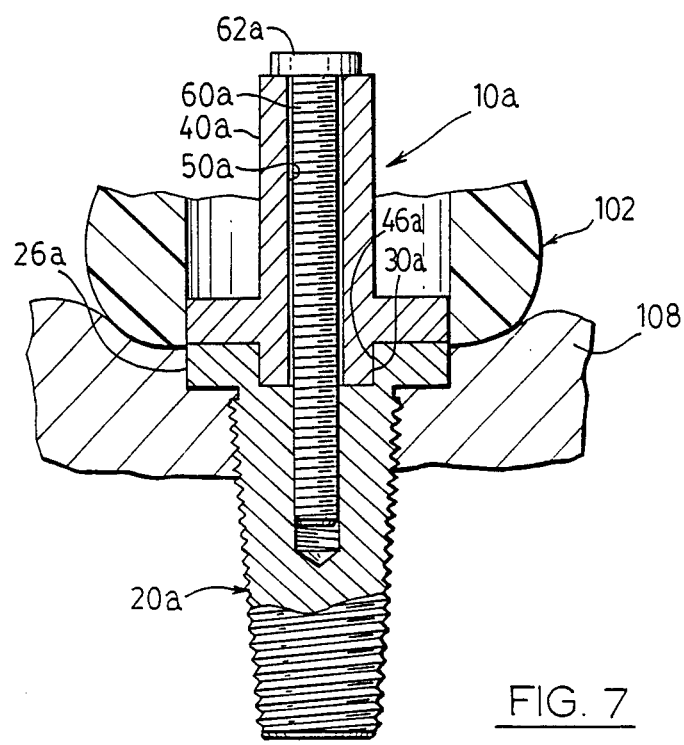
FIG. 7 represents a sectional view of an alternative embodiment of the device particularly adapted to support a single artificial tooth.

An alternative embodiment of the invention is depicted in FIG. 7 in which the device 10a is shown in use to connect a single artificial tooth to the jaw 108. Because only one device is required to anchor a single tooth, modification of the design although not strictly necessary may be desirable since the cooperative anchoring by a plurality of devices is no longer present. In this particular embodiment, the abutment 40a has been modified to resemble more closely a peg having a diameter which essentially accommodates the bore 50a. By reducing the diameter of the abutment 40a as compared with abutment 40 (FIG. 4), the artisan is provided with enhanced flexibility in the application of the tooth thereon which may be sculpted in situ from a bulk of plastic adhered to the abutment by an adhesive. In this embodiment, the diameter of the head 26a of implant 20a has been increased, and consequently, also the diameter of the base of abutment 40a has also been increased to enhance the stability of the anchored device. The protrusion 46a and recess 30a may assume a configuration similar to that depicted in FIGS. 1 and 2. It will be noted that, in this particular arrangement, the head 62a of connecting screw 60a abuts the abutment, once fully engaged in the bore 50a, since the connecting screw is not engaged entirely in the body of the abutment.

Alternative embodiments of the invention are contemplated. It is to be realized that the device is not limited to the requirement that the abutment bear the protrusion and the implant define the recess, since the protrusion may be located on either element provided the other element defines the recess. Furthermore, it will be appreciated that the tongue and groove may assume any configuration aside from one having circular cross-section, where due consideration is given to the aim of providing means for resisting rotation about the protrusion.

Figure 8:
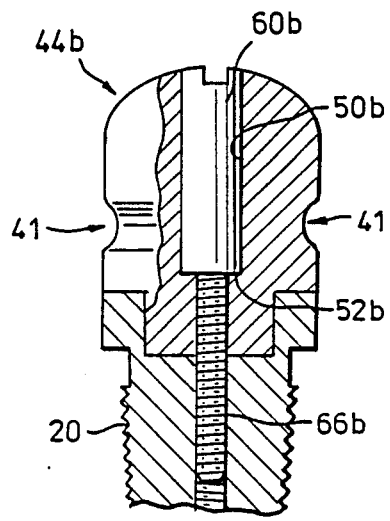
FIG. 8 represents an embodiment of the device similar to that illustrated in FIGS. 1 and 2 but embodying an abutment of different configuration.

Also, the abutment may be shaped differently from that shown in FIGS. 1 and 7. FIG. 8 illustrates a preferred modification of the abutment, in which abutment 40b defines an annular recess or "waist" 41 while retaining the domed upper surface 44b and, hence, substantially retaining the benefits accruing to such a shape, as described previously. Using abutment 40b, it is possible to fashion a prosthesis which defines a recess complementary to the abutment, allowing the prosthesis to "snap" onto the abutment and be retained by it. With such an arrangement, the abutment-engaging region of the prosthesis should be formed from resilient material to accommodate the abutment retainably. Acrylics and the various resins commonly used to make artificial teeth should possess the required resiliency. Prosthesis may be formed of non-resilient material, however, provided they bear resilient material at the areas to be coupled with the abutment.

Connection of abutment 40b to implant 20 is similar by design to connection of abutment 40 to implant 20 (FIGS. 1-4). As can be seen in FIG. 8, the abutment 40b defines a centrally located bore 50b extending through the abutment and defining a seat 52b. Connecting screw 60b couples the abutment and implant by seating against seat 52b once the shaft 66b is threadably engaged in the implant. Since in this embodiment there is no need to provide for accommodation of a retaining screw by the abutment, the connection screw 60b may occupy the entire length of the abutment bore 50b.

Figure 9:
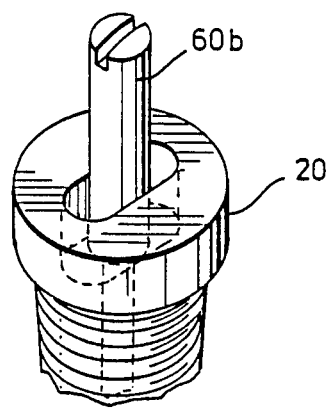
FIG. 9 represents a perspective view of another alternative embodiment of the device adapted to support a single artificial tooth.

In accordance with another alternative embodiment shown in FIG. 9, the connection screw 60b and implant 20 may be used, in the absence of any abutment, as a device for connection a single tooth to the jaw. The screw 60b is simply threaded into the implant to act as an abutment or post onto which a tooth may be sculptured in situ as described previously with reference to FIG. 7.

While particular mention has been made to the use of the device in connecting teeth to jaws, it will be appreciated that the ability of the present invention to anchor prosthesis to bone is useful in other environments, examples of which include the connection of artificial limbs to the body and connection of prosthetic ears and eyes to the head. Where the implant is to be anchored in the skull, the design of the implant is modified in view of the thickness of the cranium.

What is claimed is:

1. A device for using and connecting a prothesis to bone, which comprises:
    an implant for integration with bone, the implant having a head defining an upper surface and an externally threaded shaft depending therefrom, the shaft tapering downwardly from the head;
    an abutment to receive the prothesis, the abutment having a lower surface complementary to the upper surface of the head of the implant, one of either of said lower surface of the abutment or said upper surface of said implant bearing a tongue and the other defining a complementary groove, said tongue and groove interfitting to prevent relative rotation therebetween, said abutment defining a first bore extending longitudinally through said abutment and along a central axis thereof and said implant defining a screw threaded second bore adapted to align with said first bore of said abutment extending longitudinally from said upper surface of said implant along a central axis of said implant, said abutment defining a seat coaxial with said first bore and superior thereto; and
    connecting means for connecting the abutment to the implant at the complementary surfaces, said connecting means comprising a bolt having a head and a screw threaded portion such that when the bolt is in its connecting position, the head of the bolt engages with said seat and the screw threaded portion engages said second bore.

2. The device of claim 1 wherein the implant is self-tapping.

3. The device of claim 2 wherein the prosthesis is a dental prosthesis.

4. The device of claim 1 wherein the abutment includes a third screw threaded bore in the area above said seat.

5. The device of claim 4 including a retaining screw adapted to engage in said third bore, said retaining screw comprising a shaft and a head, the length of the screw being such that when said shaft is received in said bore, said head abuts said abutment.

6. The device of claim 5 wherein said abutment has a part-spherical dome shape.

7. The device of claim 1 wherein said abutment has a part-spherical dome shape and defines a waist.

8. The device of claim 6 wherein the abutment and implant are machined from titanium alloy.

9. A device for use in connecting a dental bridge within the oral cavity which comprises
    an implant for integration with mandibular bone having a head providing an upper planar surface with a recess therein and an externally screw-threaded shaft depending from the head, and tapering downwardly from the head, the implant defining a first screw-threaded bore extending longitudinally from said recess and along the central axis of the implant;
    an abutment for receiving the dental bridge, the abutment having a cylindrical portion having a lower planar surface with a protrusion extending therefrom whereby the lower surface is complementary to the upper surface of the head of the implant, and an upper part-spherical domed surface, the abutment defining a second bore extending longitudinally through said abutment and along a central axis thereof such that when the implant and the abutment are mated at their respective upper and lower surfaces, said first bore and said second bore are aligned; and connecting means for connecting the abutment to the implant comprised of a screw threaded element capable of being positioned within said first and second bores to effect said connection.

10. The device of claim 9 wherein the implant is self-tapping

11. The device of claim 10 wherein the abutment and implant are machined from titanium alloy.

12. A device for use in connecting an artificial tooth within the oral cavity which comprises an implant for integration with mandibular bone having a head providing an upper planar surface with a recess therein and an externally screw-threaded shaft depending from the head, and tapering downwardly from the head, the implant defining a first screw-threaded bore extending longitudinally from said recess and along the central axis of the implant;

an abutment for receiving the dental bridge, the abutment having a cylindrical portion having a lower planar surface with a protrusion extending therefrom whereby the lower surface is complementary to the upper surface of the head of the implant, and peg means extending from the cylindrical portion the peg means having a diameter generally less than the diameter of the cylindrical portion from which it extends, the abutment defining a second bore extending longitudinally through said abutment and along a central axis thereof such that when the implant and the abutment are mated at their respective upper and lower surfaces, said first bore and said second bore are aligned; and connecting means for connecting the abutment to the implant comprised of a screw threaded element capable of being positioned within said first and second bores to effect said connection.

* * * * *